United States Patent [19]

Poss et al.

[11] Patent Number: 5,234,923
[45] Date of Patent: Aug. 10, 1993

[54] SUBSTITUTE INDOLE AND BENZIMIDAZOLE DERIVATIVES

[75] Inventors: Michael A. Poss, Lawrenceville, N.J.; Karnail S. Atwal, Newtown, Pa.

[73] Assignee: E. R. Squibb & Sons, Inc., Princeton, N.J.

[21] Appl. No.: 808,410

[22] Filed: Dec. 16, 1991

[51] Int. Cl.[5] .............. A61K 31/505; C07D 491/048; C07D 491/052; C07D 239/20
[52] U.S. Cl. .................... 514/269; 514/256; 514/259; 514/260; 514/270; 514/272; 514/273; 514/274; 514/275; 544/117; 544/122; 544/123; 544/243; 544/244; 544/278; 544/279; 544/280; 544/284; 544/295; 544/300; 544/310; 544/315; 544/316; 544/317; 544/318; 544/319; 544/320; 544/321; 544/322; 544/331; 544/333
[58] Field of Search .............. 544/122, 123, 157, 243, 544/244, 278, 279, 284, 285, 286, 287, 300, 310, 315, 316, 321, 331, 332, 333, 334, 335, 117, 280, 295, 317, 318, 319, 320, 322; 514/256, 260, 269, 270, 274, 275, 259, 273; 540/490, 542, 545, 552

[56] References Cited

U.S. PATENT DOCUMENTS

| | | | |
|---|---|---|---|
| 4,340,598 | 7/1982 | Furukawa et al. | 548/337 |
| 4,355,040 | 10/1982 | Furukawa et al. | 548/342 |
| 4,582,847 | 4/1985 | Furukawa et al. | 514/400 |
| 4,812,462 | 3/1989 | Blankley et al. | 514/303 |
| 4,816,463 | 3/1989 | Blankley et al. | 546/82 |
| 4,820,843 | 4/1989 | Aldrich et al. | 548/252 |
| 4,855,301 | 8/1989 | Atwal et al. | 514/269 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |

FOREIGN PATENT DOCUMENTS

| | | |
|---|---|---|
| 253310 | 7/1987 | European Pat. Off. |
| 324377 | 1/1989 | European Pat. Off. |
| 323841 | 7/1989 | European Pat. Off. |
| 411766 | 6/1990 | European Pat. Off. |

OTHER PUBLICATIONS

Karnail S. Atwal et al., "Substituted 1,4-Dihydropyrimidines, 3, Synthesis of Selectively Functionalized 2-Hetero-1,4 dihydropyrimidines", *J. Org. Chem.*, 1989, 54, pp. 5898-5907.

Peter Bühlmayer et al., "Nonpeptidic Angiotensin II Antagonists: Synthesis and in Vitro Activity of a Series of Novel Naphthalene and Tetrahydronaphthalene Derivatives", *J. Med. Chem.*, 1991, 34, pp. 3105-3114.

Primary Examiner—Mukund J. Shah
Assistant Examiner—Y. N. Gupta
Attorney, Agent, or Firm—Ellen K. Park

[57] ABSTRACT

Novel compounds are disclosed having the formula

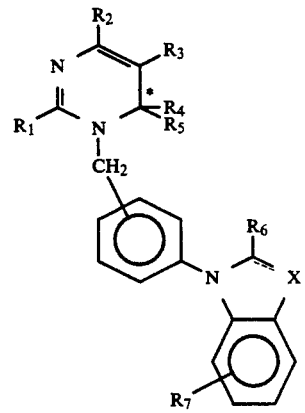

I or its isomer

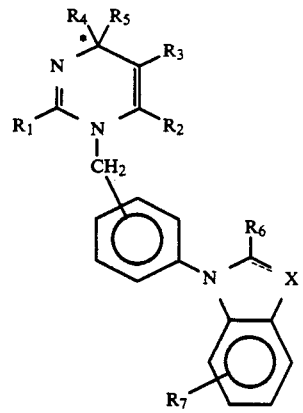

I' wherein $R_1$, $R_2$, $R_3$, $R_4$, $R_5$, $R_6$, $R_7$ and X are as defined herein. These compounds inhibit the action of angiotensin II and are useful, therefore, for example, as antihypertensive agents.

7 Claims, No Drawings

SUBSTITUTE INDOLE AND BENZIMIDAZOLE DERIVATIVES

FIELD OF THE INVENTION

The present invention relates to novel substituted indole and benzimidazoles which are useful as antihypertensive agents.

SUMMARY OF THE INVENTION

In accordance with the present invention, novel compounds which inhibit the action of the hormone angiotensin II are disclosed. These compounds are of the general formula

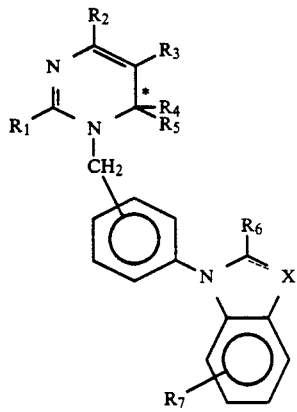

I and its isomer

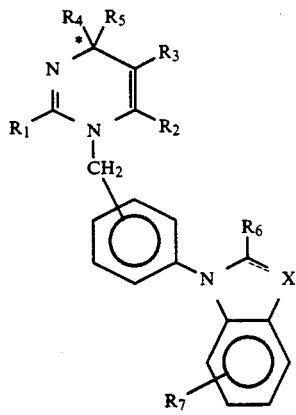

I' and pharmaceutically acceptable salts thereof wherein X is —N— or

when X is —N—, the double bond is always present;

$R_1$ is alkyl, alkenyl or alkynyl or an alkyl, alkenyl or alkynyl group substituted with F or —$CO_2R_8$; cycloalkyl; (cycloalkyl)alkyl of 4 to 10 carbon atoms; (cycloalkyl)alkenyl or (cycloalkyl)alkynyl of 5 to 10 carbon atoms; —$NR_{11}R_{12}$; —$(CH_2)_mZ(CH_2)_nR_{14}$; benzyl or benzyl substituted with 1 or 2 halogens, alkoxy of 1 to 4 carbon atoms, alkyl of 1 to 4 carbon atoms, haloalkyl or nitro; —$SR_{15}$; or —$OR_{15}$;

$R_2$ is halogen, —CN, —$OR_{15}$, —$SR_{15}$, —$COR_{15}$, $R_{16}$, ($R_{16}O$)alkyl, ($R_{16}S$)alkyl, —$CO_2R_{17}$ or (substituted amino)alkyl;

$R_3$ is —CN, —$NO_2$,

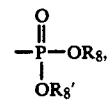

—$CONR_{11}R_{12}$, ($R_{15}OCO$)alkyl, ($R_{16}O$)alkyl, ($R_{16}S$)alkyl, ($R_{16}CO$)alkyl, —$CO_2R_{17}$, $R_{18}$, —$COR_{18}$, —$SO_2R_{18}$ or ($R_{18}OC$)alkyl; or $R_2$ and $R_3$ taken together are

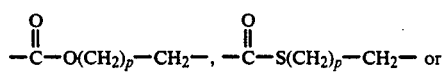

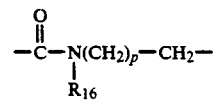

to form a 5— to 7-membered ring with the carbon atoms to which they are attached; or $R_2$ and $R_2$ taken together with the carbon atoms to which they are attached form an aryl or heterocyclo group;

$R_4$ and $R_5$ are independently selected from hydrogen, alkyl, alkenyl, alkynyl, aryl, arylalkyl, cycloalkyl, (cycloalkyl)alkyl, heterocyclo, (heterocyclo)alkyl, haloalkyl or —$CO_2R_8$;

or $R_4$ and $R_5$ taken together with the carbon atom to which they are attached form a 5— to 7—membered carbocyclic ring which may have another 5— to 7—membered ring fused thereto; or $R_4$ and $R_5$ together with the carbon atom to which they are attached form a carbonyl or a thiocarbonyl group;

$R_6$ and $R_6'$ are independently selected from hydrogen, alkyl, aryl, cycloalkyl, arylalkyl, haloalkyl, —$CO_2R_8$, —$NHSO_2CF_3$,

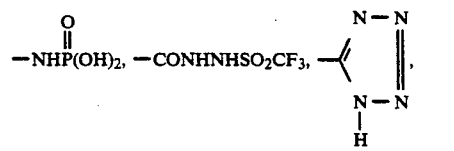

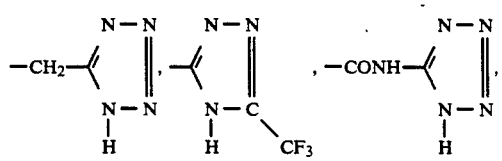

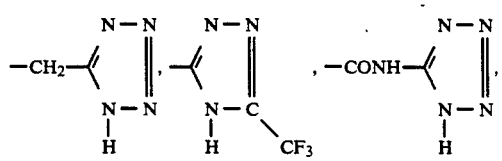

-continued

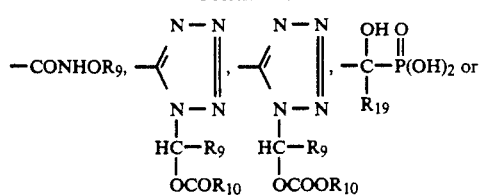

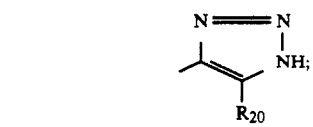

$R_7$ is an acid moiety such as hydrogen, $-CO_2R_8$, $-NHSO_2CF_3$,

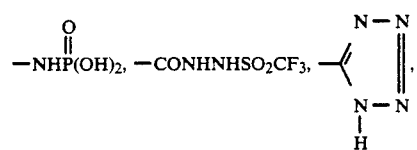

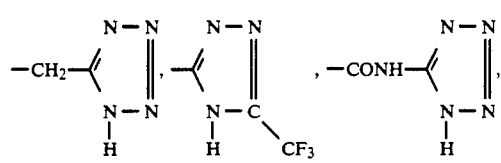

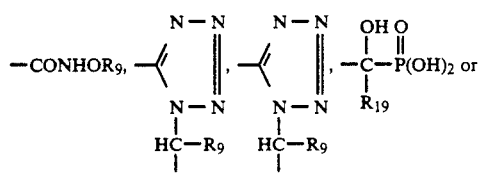

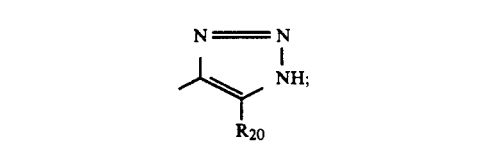

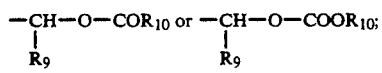

$R_8$ and $R_8'$ are independently hydrogen, alkyl, perfluoroalkyl of 1 to 8 carbon atoms, cycloalkyl of 3 to 6 carbon atoms, phenyl, benzyl,

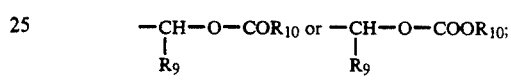

$R_9$ is hydrogen, alkyl, aryl, arylalkyl or cycloalkyl;
$R_{10}$ is alkyl, aryl, alkylaryl, arylalkyl or cycloalkyl;
$R_{11}$ and $R_{12}$ are independently hydrogen, alkyl of 1 to 6 carbon atoms, benzyl, α-methylbenzyl, or taken together with the nitrogen atom to which they are attached form a ring of the formula

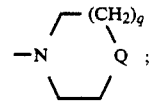

$R_{13}$ is hydrogen, alkyl of 1 to 6 carbon atoms, cycloalkyl of 3 to 6 carbon atoms, phenyl or benzyl;

$R_{14}$ is hydrogen; alkyl of 1 to 6 carbon atoms; cycloalkyl; alkenyl or alkynyl of 2 to 4 carbon atoms; or the above alkyl, cycloalkyl, alkenyl or alkynyl group optionally substituted with F or $-CO_2R_8$;

$R_{15}$ is alkyl, alkenyl, alkynyl, aryl, arylalkyl, cycloalkyl, (cycloalkyl)alkyl, heterocyclo, (heterocyclo)alkyl or haloalkyl;

$R_{16}$ is hydrogen, alkyl, alkenyl, alkynyl, aryl, arylalkyl, cycloalkyl, (cycloalkyl)alkyl, heterocyclo, (heterocyclo)alkyl or haloalkyl;

$R_{17}$ is hydrogen, alkyl, alkenyl, alkynyl, perfluoroalkyl of 1 to 8 carbon atoms, cycloalkyl, aryl, arylalkyl, (cycloalkyl)alkyl, heterocyclo, (heterocyclo)alkyl, haloalkyl, $$-\underset{R_9}{CH}-O-COR_{10} \text{ or } -\underset{R_9}{CH}-O-COOR_{10};$$

$R_{18}$ is aminoalkyl, (substituted amino)alkyl; or $R_{16}$;
$R_{19}$ is hydrogen, alkyl of 1 to 5 carbon atoms or phenyl;
$R_{20}$ is $-CN$, $-NO_2$ or $-CO_2R_8$;
Q is $-CH_2$, $-O-$, or $-NR_9$;
Z is $-O-$, $-S-$ or $-NR_{13}$;
m is an integer of 1 to 5;
n is an integer of 1 to 5;
p is 0, or the integer 1 or 2; and
q is 0, or the integer 1.

DETAILED DESCRIPTION OF THE INVENTION

The present invention relates to the compounds of formula I and I' and to pharmaceutical compositions employing such compounds and to methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 10 carbon atoms. Alkyl groups having 1 to 4 carbon atoms are preferred.

The terms "alkenyl" and "alkynyl" refer to both straight and branched chain groups. Those groups having 2 to 10 carbon atoms are preferred.

The term "cycloalkyl" refers to groups having 3 to 8 carbon atoms.

The term "alkoxy" refers to groups having 1 to 8 carbon atoms. Alkoxy groups having 1 to 3 carbon atoms are preferred.

The term "halogen" refers to fluorine, chlorine, bromine and iodine with fluorine and chlorine being preferred.

The term "haloalkyl" refers to such alkyl groups described above in which one or more hydrogens have been replaced by chloro, bromo or fluoro groups such as trifluoromethyl, pentafluoroethyl, 2,2,2-trichloroethyl, chloromethyl, bromomethyl, etc., trifluoromethyl being preferred.

The term "aryl" refers to phenyl or naphthyl or phenyl or naphthyl substituted with substituents selected from halogen, alkyl, alkoxy, carboxy, alkylthio, hydroxy, alkanoyl, nitro, amino, alkylamino, dialkylamino or trifluoromethyl groups. The aryl group is attached by way of an available carbon atom or is fused when $R_2$ and $R_3$ taken together with the carbon atoms to which they are attached form the aryl ring. Preferred aryl groups are phenyl and monosubstituted phenyl and phenyl is most preferred.

The term "heterocyclo" refers to fully saturated or unsaturated rings of 5 or 6 atoms containing one to four nitrogen atoms, or one oxygen atom, or one sulfur atom, or one oxygen atom and one or two nitrogen atoms, or one sulfur atom and one or two nitrogen atoms. The heterocyclo ring is attached by way of an available carbon atom or is fused when $R_2$ and $R_3$ taken together with the carbon atoms to which they are attached, form the heterocyclic ring. Preferred monocyclic heterocyclo groups include 2- and 3-thienyl, 2- and 3- furyl, 2- , 3- and 4- pyridyl, and imidazolyl. The heterocycle may also have a substituent selected from alkyl of 1 to 4 carbons, carboxy, alkoxy of 1 to 4 carbons and alkylthio of 1 to 4 carbons on an available carbon. The term heterocyclo also includes bicyclic rings wherein the five or six membered ring containing oxygen, sulfur and nitrogen atoms as defined above is fused to a benzene ring and the bicyclic ring is attached by way of an available carbon atom in the benzene ring. Preferred bicyclic heterocyclo groups include 4, 5, 6 or 7- indolyl, 4, 5, 6 or 7- isoindolyl, 5, 6, 7 or 8- quinolinyl, 5, 6, 7 or 8- isoquinolinyl, 4, 5, 6, or 7- benzothiazolyl, 4, 5, 6 or 7- benzoxazolyl, 4, 5, 6 or 7- benzimidazolyl, 4, 5, 6 or 7- benzoxadiazolyl, and 4, 5, 6 or 7- benzofuranyl. Preferred fused heterocycles include thienyl, furyl, pyridyl and imidazolyl, optionally substituted as described above.

The term "substituted amino" refers to a group of the formula $-NZ_1Z_2$ wherein $Z_1$ is hydrogen, alkyl, or aryl-$(CH_2)_p-$ and $Z_2$ is alkyl or aryl-$(CH_2)_p-$ or $Z_1$ and $Z_2$ taken together with the nitrogen atom to which they are attached are 1- pyrrolidinyl, 1- piperidinyl, 1- azepinyl, 4- morpholinyl, 4-thiamorpholinyl, 1- piperazinyl, 4- alkyl- 1- piperazinyl, 4- arylalkyl- 1- piperazinyl, 4- diarylalkyl- 1- piperazinyl, or 1- pyrrolidinyl, 1- piperidinyl, or 1- azepinyl substituted with alkyl, alkoxy, alkylthio, halo, trifluoromethyl or hydroxy.

To prepare the compounds of formula I a compound of the formula

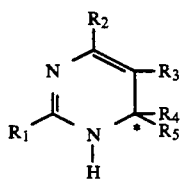

is coupled with a compound of the formula

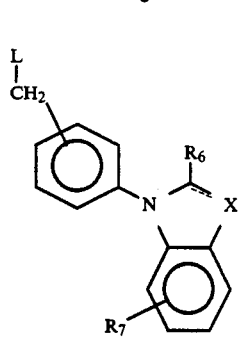

wherein L is a leaving group such as a halogen, in the presence of a base such as potassium hexamethyldisilazane, in an organic solvent such as tetrahydrofuran or dimethylformamide.

Compounds of formula II wherein $R_2$ is a halogen and $R_3$ is $-CO_2R_{17}$ can be prepared by first reacting an amidine of the formula

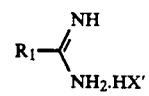

(wherein X' is a halogen) with an olefin of the formula

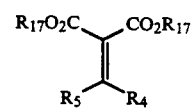

in an organic solvent, such as dimethylformamide, and in the presence of a base, such as potassium carbonate to provide a pyrimidine of the formula

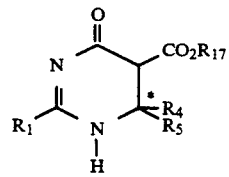

The pyrimidine of formula VI can thereafter be heated in the presense of a chlorinating agent, e.g., phosphorus oxychloride to provide the intermediates of formula II where $R_2$ is chloro and $R_3$ is $-CO_2R_{17}$. Compounds of formula II where $R_2$ is a halogen other than chloro can be made in a similar fashion.

To provide the intermediates of formula II where $R_2$ is other than halogen, the amidine of formula IV can be reacted with an olefin of the formula

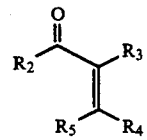

in the presence of base such as sodium bicarbonate, and in an organic solvent such as dimethylformamide to provide an intermediate of the formula

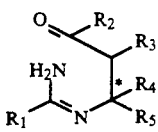

VIII

Intermediate VIII can thereafter be cyclized, e.g., by heating in the presence of an acid, such as p-toluenesulfonic acid, and in an organic solvent, such as benzene or dimethylformamide, to provide compounds of formula II where $R_2$ is other than halogen.

Compounds of formula II, where $R_4$ and $R_5$ together with the carbon atom to which they are attached form a carbonyl group, can be prepared by reacting compounds of the formula

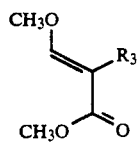

IX with an amidine of formula IV in the presence of a base such as sodium bicarbonate or sodium acetate.

Alternatively, compounds of formula II where $R_4$ and $R_5$ are a carbonyl group can be prepared by reacting a compound of the formula

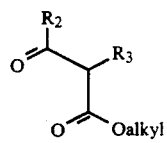

X with an amidine of formula IV in the presence of a base such as sodium bicarbonate or sodium acetate in a polar solvent such as ethanol or dimethylformamide.

Preferably, compounds of formula II where —$R_4$ and $R_5$ together form a carbonyl group and $R_2$ and $R_3$ together with the carbon atoms to which they are attached form a fused aryl group, can be prepared by reacting anthranilamide with an acyl halide such as valeryl chloride ($R_1$=n—Bu) to form a compound of formula

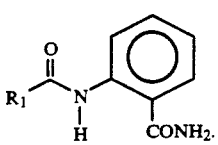

Xa

Compounds of formula Xa are then reacted in an organic solvent such as toluene with a base such as pyridine in the presence of a dehydrating agent such as molecular sieves to form the compounds of formula II.

Other dihydropyrimidines of formula II can be prepared by methods described in the literature, e.g., K. Atwal et al., *J. Org. Chem.*, Vol. 54, p. 5898 (1989) and references cited therein.

Compounds of formula III can be prepared by coupling a compound of the formula

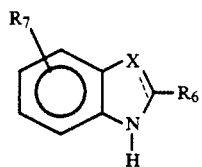

XI with a compound of the formula

XII where Br is bromine in a polar solvent such as pyridine and in the presence of a catalyst such as copper oxide, to provide compounds of the formula

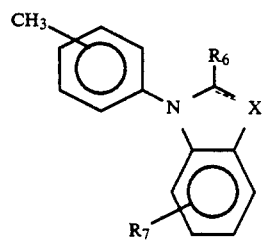

XIII

A leaving group, L, for example a halogen can be added by known methodology to provide compounds of the formula

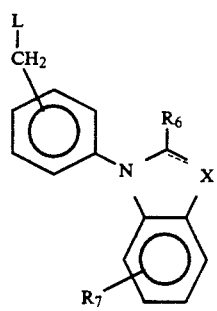

IIIa

Compounds of formula XI where X is

and the double bond is present can be prepared by known techniques such as those described in *J. Heterocyclic Chem.*, 25, 1 (1988).

Compounds of formula XI where X is nitrogen and the double bond is present can be prepared as described by Mathias et al., *Synthetic Communications*, 5, 461–469 (1975).

Alternatively compounds of formula III can be prepared by reacting a compound of the formula XI with a compound of the formula

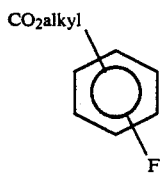

XV in the presence of a base such as potassium carbonate, and in an organic solvent such as dimethylformamide, to provide a compound of the formula

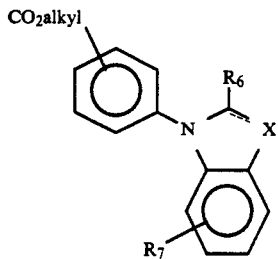

XVI

Compound XVI can thereafter be treated with a reducing agent such as lithium borohydride, in an organic solvent such as methanol, to provide a compound of the formula

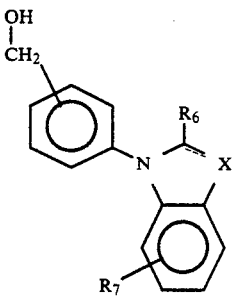

XVII

Conversion of compounds of formula XVII to compounds of formula III may be accomplished by known methodology.

Alternatively compounds of formula I where $R_6$ is tetrazolyl are prepared by substituting a compound of the formula

XVIII for the compound of formula XI in the above methodology. Methods for the preparation of compounds of formula XVIII have been described in Rocz. Chem. 51, 1783 (1977). Thereafter, the product is treated with an azide such as tributyltinazide in an organic solvent such as xylene, to convert the —CN to the desired tetrazolyl ($R_6$) group. As would be understood by those skilled in the art, this methodology is also readily applicable to the preparation of the indole derivatives above wherein $R_7$ is tetrazolyl.

The compounds of formula I and I' can have an asymmetric center within the pyrimidine ring as represented by the asterisk (*). Also, any of the R groups can have an asymmetric center. Thus, the compounds of formula I can exist in diastereomeric forms or in mixtures thereof. The above-described processes can utilize racemates, enantiomers or diastereomers as starting materials. When diastereomeric products are prepared, they can be separated by conventional chromatographic or fractional crystallization methods.

When preparing the compounds of the instant invention wherein the substituent groups contain one or more reactive functionalities such as hydroxy, amino, tetrazolyl, carboxyl, mercapto or imidazolyl groups, it may be necessary to protect these groups during the reactions in which they are used. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of the present invention are those wherein

R is an alkyl of 3 to 5 carbons;

$R_2$ is hydrogen, alkyl, haloalkyl or chloro; and $R_3$ is —$CO_2R_{17}$; or $R_2$ and $R_3$ together with the carbon atoms to which they are attached form a fused aryl ring;

$R_4$ is hydrogen and $R_5$ is alkyl; or $R_4$ and $R_5$ together with the carbon atom to which they are attached form a carbonyl group;

$R_6$ is hydrogen, —$CO_2H$ or tetrazolyl;

$R_7$ is hydrogen, 7-tetrazolyl or 7—$CO_2H$;

X is $$-\underset{\underset{R_6'}{|}}{C}-,$$

where $R_6'$ is hydrogen, —$CO_2H$ or tetrazolyl; or —N; and the double bond is present.

Most preferred are compounds of formula I wherein

R is n-butyl;

$R_2$ is hydrogen, —$CF_3$ or chloro and $R_3$ is —$CO_2R_{17}$;

$R_4$ is hydrogen and $R_5$ is methyl; or $R_4$ and $R_5$ together with the carbon atom to which they are attached form a carbonyl group;

$R_6$ is tetrazolyl;

$R_7$ is hydrogen;

X is $$-\underset{\underset{R_6'}{|}}{C}-,$$

where $R_6'$ is hydrogen; and the double bond is present: and connection from the dihydropyrimidinyl portion is via the para-position of the benzene ring.

The present compounds of formula I and I' inhibit the action of the hormone angiotensin II (A-II) and are therefore useful, for example, as antihypertensive agents.

The action of the enzyme renin on angiotensinogen, a pseudoglobulin in blood plasma, produces A-II. Angiotensin I is converted by angiotensin converting enzyme (ACE) to A-II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy. In addition, in view of the role of these compounds in the reninangiotensin system described above, the A-II antagonist compounds disclosed herein are also expected to be useful for the same or similar indications which have developed for ACE inhibitors.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I and I' can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I or I' is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

2-Butyl-3-[[4-[2-(2H-tetrazol-5-yl)-1H-indol-1-yl]phenyl]methyl]-4(3H)-quinazolinone, monolithium salt

A. 1H-Indole-2-carboxamide

Indole-2-carboxylic acid (10.26 g, 63.7 mmol) was dissolved in dichloromethane (125 mL) and oxalyl chloride (39.8 mL of a 2.0M solution in methylene chloride) was slowly added dropwise to the reaction at room temperature. Upon full addition, dimethylformamide (0.32 mL) was added and the reaction was stirred for two hours. After two hours, the reaction solution was transparent yellow in color. Ammonia gas was then bubbled into the reaction for 25 minutes and the reaction was stirred at room temperature for an additional 30 minutes. The reaction was then partitioned between water and ethyl acetate. The organic phase was washed with saturated ammonium chloride, then dried and concentrated to provide crude amide (9.53 g), which was used in the next step without further purification.

B. 1H-Indole-2-carbonitrile

The title A compound (8.5 g, 53.1 mmol) was suspended in 1,4 dioxane (110 mL) and pyridine (10.74 mL). The solution was then cooled to less than 10° C. and trifluoroacetic anhydride (11.99 mL, 84.9 mmol) was slowly added to the reaction. Upon full addition, the reaction was stirred at room temperature for 18 hours. The reaction was then slowly quenched with water and extracted with ethyl acetate and the organic phase was dried and concentrated. The crude solid was purified by flash chromatography (silicon dioxide, 95:5 hexane:ethyl acetate) to provide pure nitrile (4.16 g, 55% over 2 steps).

C. 4-(2-Cyano-1H-indol-1-yl)benzoic acid, ethyl ester

The title B compound (4.15 g, 29.2 mmol) and freshly ground potassium carbonate (8.1 g, 58.4 mmol) were placed in anhydrous dimethylformamide (60 mL). Ethyl-4-fluorobenzoate (14.73 g, 87.6 mmol) was then added via syringe at room temperature and the reaction was then heated to 110° C. for 40 hours. The reaction was then partitioned between ethyl acetate and saturated ammonium chloride and the organic phase was dried and concentrated. The crude ester was purified by flash chromatography (silicon dioxide, 96:4 Hexane:ethyl acetate) to provide pure ester (5.17 g, 61%).

D. 1-[4-(Hydroxymethyl)phenyl]-1H-indole-2-carbonitrile

Lithium aluminum hydride (61.0 mL of 1.0M solution in ethyl ether) was added to silica gel (22.0 g) that had been vacuum dried at 150° C. for 1.5 hours and cooled to room temperature under vacuum. Ethyl ether (60 mL) was then added and the reaction was stirred at room temperature for 1.25 hours. The reaction was then cooled to −15° C and the title C compound was added. The reaction gradually warmed to −5° C. and was stirred at this temperature for one hour. TLC indicated some starting material was still present. The reaction was then warmed to 5° C. for 1.5 hours and the reaction was found to be complete. The reaction was then cooled to 0° C. and slowly quenched with saturated ammonium chloride. The reaction was then diluted in ethyl acetate and 1N hydrochloric acid and filtered, washing the residue thoroughly with ethyl acetate. The organic filtrate was separated, dried and concentrated and the crude oil was purified by flash chromatography (silicon dioxide, 80:20 hexane:acetone) to provide pure alcohol (1.65 g, 67%).

E. 1-[4-(Bromomethyl)phenyl]-1H-indole-2-carbonitrile

The title D compound (1.92 g, 7.73 mmol) was dissolved in dry methylene chloride (38 mL) and carbon tetrabromide (2.82 g, 8.5 mmol) was added at room temperature. The reaction was then cooled to 0° C. and triphenylphosphine (2.43 g, 9.28 mmol) was added all at once. The reaction was stirred at 0° C. for five minutes, then gradually warmed to room temperature. The reaction was then concentrated and purified by flash chromatography (silicon dioxide, 95:5 hexane:acetone) to provide pure bromide (2.15 g, 89%).

F. 2-Butyl-4(3H)-quinazolinone

1. 2-(1-Oxopentyl)amino]benzamide

Valeryl chloride (6.0 mL, 50 mmol) was added to a mixture of anthranilamide (6.8 g, 50 mmol) and triethylamine (7.0 mL, 50 mmol) in tetrahydrofuran (100 mL) at 25° C. A rapid, exothermic reaction was observed, but no external cooling was required to prevent reflux. The mixture was stirred at ambient temperature for 19 hours, after which it was poured into excess aqueous sodium bicarbonate solution, extracted with ethyl acetate, dried (magnesium sulfate), and concentrated in vacuo. The residue was triturated with hexane/ether to give the title compound as a tan solid (9.9 g, 90%); m.p. 119°–120° C.

2. 2-Butyl-4(3H)-quinazolinone

A mixture of the title 1 compound (9.2 g, 42 mmol), toluene (200 mL) and pyridine (150 mL) was heated to reflux, after which molecular sieves (3 Å 100 mL) were added. The mixture was heated at reflux for two hours, more molecular sieves (100 mL) were added and reflux was continued for a total of 18 hours. The mixture was then filtered and the filtrate was concentrated in vacuo. The residue was dissolved in chloroform (500 mL), filtered again (millipore), and reconcentrated. The residue was triturated with hexanes to give the title compound as a white solid (6.8 g, 80%); m.p. 153°–155° C.

G. 1-[4-[[2-Butyl-4-oxo-3(4H)-quinazolinyl]-methyl]-phenyl]-1H-indole-2-carbonitrile The title F compound (0.281 g, 1.39 mmol) and finely ground cesium carbonate (0.977 g, 3.02 mmol) and the title E compound (0.360 g, 1.16 mmol) were combined in anhydrous dimethylformamide (2.3 mL) and the reaction was stirred at room temperature for 20 hours. The reaction was then partioned between ethyl acetate and saturated ammonium chloride and the organic phase was dried and concentrated. The crude nitrile was purified by flash chromatography (silicon dioxide, 80:20 hexane:ethyl acetate) to provide purified nitrile (0.389 g, 77%).

H. 2-Butyl-3-[[4-[2-(2H-tetrazol-5-yl)-1H-indol-1-yl]phenyl]methyl]-4(3H)-quinazolinone, monolithium salt The title G compound (0.374 g, 0.865 mmol) and tributyltin azide (1.15 g, 3.46 mmol) were dissolved in dry xylene (1.75 mL) and the reaction was heated to 100° C. for 16 hours. The reaction was then concentrated and the crude oil was purified by flash chromatography (silicon dioxide, 98:1:1 methylene chloride: methanol:acetic acid) to provide tetrazole (0.324 g, 79%). 1.0M lithium hydroxide (0.78 mL, 0.78 mmol) was added to the purified tetrazole and water (3.0 mL) and methanol (2.0 mL) were added in order to effect a solution. The pale yellow solution was then placed on an HP-20 column and eluted with 0–40% acetonitrile:-water (in 5% increments, 250 mL each). The product was collected, passed through a millipore filter and lyophilized to provide 178 mg of 99.1% pure white solid (77%).

Analysis: calc for $C_{28}H_{24}N_7Li_1O_1 \cdot 3.0\ H_2O$: C, 62.7g; H, 5.65; N, 18.31.

Found: C, 63.06; H, 5.49; N, 18.35.

EXAMPLE 2

2-Butyl-6-chloro-1,4-dihydro-4,4-dimethyl-1-[[4-[2-(2H-tetrazol-5-yl)-1H-indol-1-yl]phenyl]methyl]-5-pyrimidinecarboxylic acid, ethyl ester, trifluoroacetate (1:1) salt

A. 2-Butyl-6-chloro-1,4-dihydro-4,4-dimethyl-5-pyrimidinecarboxylic acid, ethyl ester

1. Pentanimidamide, monohydrochloride [Reference: M. Yanai et al., *J. Pharm. Soc.*, Japan 1941, 61, 99–107; *Chem. Abstract* 36, 479]

Ammonia gas was slowly bubbled through absolute ethanol (125 mL) at 0° C. (ice bath) for 20 minutes. To the resulting solution was added pentanimidic acid, ethyl ester, monohydrochloride (25 g, 151 mmol) in one portion. The reaction mixture was stirred at 0° C. for 30 minutes to give a clear solution. It was allowed to stand at 0° C. for three more hours and the solvent was evaporated under reduced pressure to yield a light yellow semisolid (22 g) which was used for the next reaction without purification.

2. 2-Butyl-6,6-dimethyl-4-oxo-1,4,5,6-tetrahydropyrimidine-5-carboxylic acid, ethyl ester To the solution of the title 1 compound (3.53 g, 25.87 mmol) in dimethylformamide (7.0 mL) at 0° C. under argon was added potassium tert-butoxide (2.57 g, 22.85 mmol). The cooling bath was removed and the resulting suspension was stirred at room temperature for 30 minutes. To the reaction mixture was added diethyl isopropylidenemalonate (4.0 g, 19.9 mmol) in dimethylformamide (5 mL). It was stirred at room temperature overnight and then heated at 70° C. for two hours. The reaction mixture was diluted with water and extracted with ethyl acetate. The combined organic extracts were washed with water, brine and dried over anhydrous magnesium sulfate. The solvent was evaporated to give a light yellow oil (4.97 g, 98.4%).

3. 6-Butyl-4-chloro-1,2-dihydro-2,2-dimethyl-5-pyrimidinecarboxylic acid, ethyl ester The reaction mixture containing the title 2 compound (3.0 g, 11.9 mmol) in phosphorus oxychloride (10 mL) was heated at 120° C. for five hours. TLC of the reaction mixture indicated the presence of some starting material Heating was continued for five more hours. The reaction mixture was cooled to room temperature and most of the phosphorus oxychloride was distilled off under vacuum. The brown residue in ethyl acetate was washed with 10% aqueous potassium carbonate, brine and dried over magnesium sulfate. The solvent was evaporated and the residue was purified by flash chromatography (ethyl acetate:hexanes/1:2 containing 0.01% triethyl amine) to give the title compound as a light yellow oil (1.03 g, 31.8%, low yield due to spillage) which solidified on standing.

B. 2-Butyl-6-chloro-1-[[4-(2-cyano-1H-indol-1-yl)phenyl]methyl]-1,4-dihydro-4,4-dimethyl-5-pyrimidinecarboxvlic acid, ethyl ester The title A compound (0.480 g, 1.92 mmol) and the title E compound of Example 1 (0.50 g, 1.61 mmol)

were placed in anhydrous dimethylformamide (3.25 mL). Freshly ground cesium carbonate (1.05 g, 3.22 mmol) was then added and the reaction was stirred at room temperature for 20 hours. The reaction was then partitioned between ethyl acetate and saturated ammonium chloride and the organic phase was washed with water, dried and concentrated. The crude oil was purified by flash chromatography (silicon dioxide, 75:25 hexane: ethyl acetate) to yield the title compound (0.677 g, 84%).

C. 2-Butyl-6-chloro-1,4-dihydro-4,4-dimethyl -1-[4-[2-(2H-tetrazol-5-yl)-1H-indol-1-yl)phenyl]methyl]-5-pyrimidinecarboxylic acid, ethyl ester, trifluoroacetate (1:1) salt The title B compound (0.641 g, 1.27 mmol) and tributyltin azide (1.69 g, 5.10 mmol) were combined in anhydrous xylene (2.6 mL) and heated at 95° C. for 34 hours. The reaction was then cooled to room temperature and concentrated. The crude oil was flash chromatographed (silicon dioxide, 91:7:2 methylene chloride: methanol: acetic acid) to provide a light yellow solid (380 mg, 55%) which was 97% pure by HPLC. A portion (250 mg) of solid was further purified by preparative HPLC (YMC S-10 ODS, 30×150 mm column, isocratic conditions, 65:35:0.01 methanol: water: trifluoroacetic acid) to provide a light yellow solid (150 mg).

Analysis: calc for $C_{29}H_{32}ClN_7O_2 \cdot 0.96\ C_2HF_3O_2 \cdot 0.8\ H_2O$; C, 55.43; H, 5.25; N, 14.63; Cl, 5.29; F, 8.17. Found: C, 55.83; H, 4.99; N, 14.06; Cl, 5.28; F, 8.15.

What is claimed is:

1. A compound of the formula

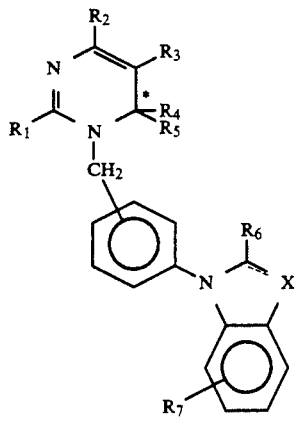

I or its isomer

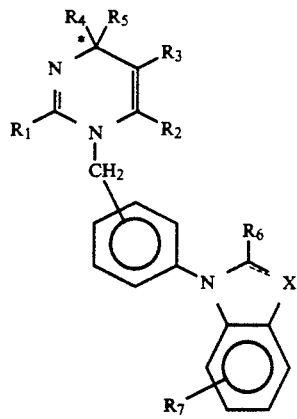

I' or a pharmaceutically acceptable salt thereof;

X is —N— or

when X is —N—, the double bond is always present;

$R_1$ is alkyl, alkenyl or alkynyl or an alkyl, alkenyl or alkynyl group substituted with F or —$CO_2R_8$; cycloalkyl; (cycloalkyl)alkyl or 4 to 10 carbon atoms; (cycloalkyl)alkenyl or (cycloalkyl)alkynyl of 5 to 10 carbon atoms; —$NR_{11}R_{12}$; —$(CH_2)_mZ(CH_2)_nR_{14}$; benzyl or benzyl substituted with 1 or 2 halogens, alkoxy of 1 to 4 carbon atoms, alkyl of 1 to 4 carbon atoms, haloalkyl or nitro; —$SR_{15}$; or —$OR_{15}$;

$R_2$ is hydrogen, —CN, —$OR_{15}$, —$SR_{15}$, —$COR_{15}$, $R_{16}$, ($R_{16}O$)alkyl, $R_{16}S$)alkyl, —$CO_2R_{17}$ or (substituted amino)alkyl;

$R_3$ is —CN, —$NO_2$,

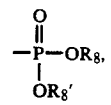

—$CONR_{11}R_{12}$, ($R_{15}OCO$)alkyl, ($R_{16}O$)alkyl, ($R_{16}S$)alkyl, ($R_{16}CO$)alkyl, —$CO_2R_{17}$, $R_{18}$, —$COR_{18}$, —$SO_2R_{18}$ or ($R_{18}OC$)alkyl; or $R_2$ and $R_3$ taken together are

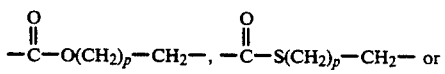

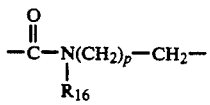

to form a heterocyclic ring with the carbon atoms to which they are attached; or $R_2$ and $R_3$ taken together with the carbon atoms to which they are attached form an aryl or heterocyclo group;

$R_4$ and $R_5$ are independently selected from hydrogen, alkyl, alkenyl, alkynyl, aryl, arylalkyl, cycloalkyl, (cycloalkyl)alkyl, heterocyclo, (heterocyclo)alkyl, haloalkyl or —$CO_2R_8$; or R4 and R5 taken together with the carbon atom to which they are attached form a 5- to 7-membered carbocyclic ring which may have another 5- to 7-membered ring fused thereto; or R4 and R5 together with the carbon atom to which they are attached form a carbonyl or a thiocarbonyl group;

R6 and R6' are independently selected from hydrogen, alkyl, aryl, cycloalkyl, arylalkyl, haloalkyl, —CO2R8, —NHSO2CF3,

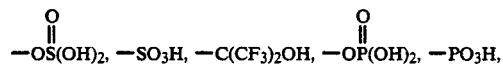

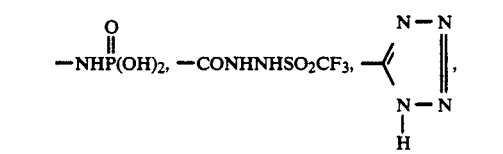

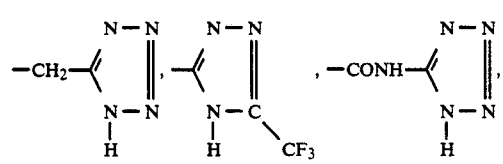

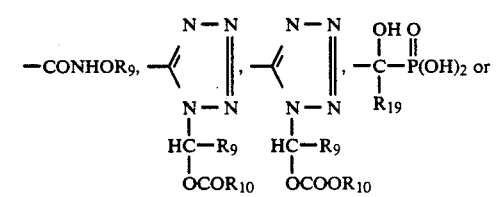

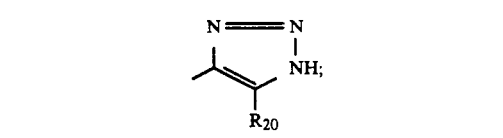

R7 is an acid moiety such as hydrogen, —CO2R8, —NHSO2CF3,

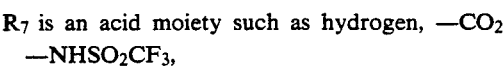

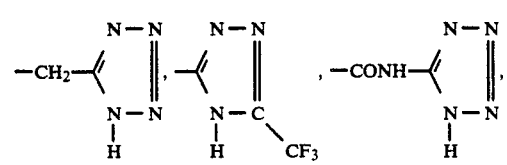

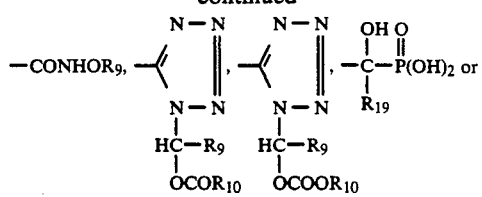

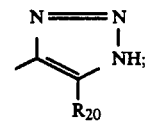

R8 and R8' are independently hydrogen, alkyl, perfluoroalkyl of 1 to 8 carbon atoms, cycloalkyl of 3 to 6 carbon atoms, phenyl, benzyl,

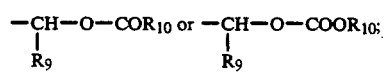

R9 is hydrogen, alkyl, aryl, arylalkyl or cycloalkyl;

R10 is alkyl, aryl, alkylaryl, arylalkyl or cycloalkyl;

R11 and R12 are independently hydrogen, alkyl of 1 to 6 carbon atoms, benzyl, α-methylbenzyl, or taken together with the nitrogen atom to which they are attached form a ring of the formula

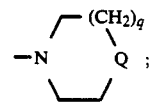

R13 is hydrogen, alkyl of 1 to 6 carbon atoms, cycloalkyl of 3 to 6 carbon atoms, phenyl or benzyl;

R14 is hydrogen; alkyl of 1 to 6 carbon atoms; cycloalkyl; alkenyl or alkynyl of 2 to 4 carbon atoms; or the above alkyl, cycloalkyl, alkenyl or alkynyl group optionally substituted with F or —CO2R8;

R15 is alkyl, alkenyl, alkynyl, aryl, arylalkyl, cycloalkyl, (cycloalkyl)alkyl, heterocyclo, (heterocyclo)alkyl or haloalkyl;

R16 is hydrogen, alkyl, alkenyl, alkynyl, aryl, arylalkyl, cycloalkyl, (cycloalkyl)alkyl, heterocyclo, (heterocyclo)alkyl or haloalkyl;

R17 is hydrogen, alkyl, alkenyl, alkynyl, perfluoroalkyl of 1 to 8 carbon atoms, cycloalkyl, aryl, arylalkyl, (cycloalkyl)alkyl, heterocyclo, (heterocyclo)alkyl, haloalkyl,

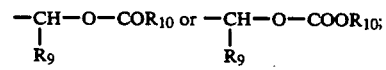

R18 is aminoalkyl, (substituted amino)alkyl; or R16;

R19 is hydrogen, alkyl of 1 to 5 carbon atoms or phenyl;

R20 is —CN, —NO2 or —CO2R8;

Q is —CH2, —O—, or —NR9;

Z is —O—, —S— or —NR13;

m is an integer of 1 to 5;

n is an integer of 1 to 5;

p is 0, or the integer 1;

q is 0, or the integer 1 wherein "aryl" refers to phenyl or naphthyl optionally substituted with substituents selected from halogen, alkyl, alkoxy, carboxy, alkylthio, hydroxy, alkanoyl, nitro, amino, alkylamino, dialkylamino or trifluoromethyl groups; and "heterocyclo" refers to fully saturated or unsaturated rings of 5 or 6 atoms containing one to four nitrogen atoms, or one oxygen atom, or one sulfur atom, or one oxygen atom and one or two nitrogen atoms, or one sulfur atom and one or two nitrogen atoms, optionally substituted with substituents selected from alkyl of 1 to 4 carbons, carboxy, alkoxy of 1 to 4 carbons and alkylthio of 1 to 4 carbons on an available carbon; bicyclic rings wherein said five or six membered ring is fused to a benzene ring, optionally substituted with substituents selected from alkyl of 1 to 4 carbons, carboxy, alkoxy of 1 to 4 carbons and alkylthio of 1 to 4 carbons on an available carbon.

2. A compounds of claim 1 wherein
$R_1$ is alkyl of 3 to 5 carbons;
$R_2$ is hydrogen, alkyl, haloalkyl or chloro; and $R_3$ is —$CO_2R_{17}$; or $R_2$ and $R_3$ together with the carbon atoms to which they are attached form a fused aryl ring;
$R_4$ is hydrogen and $R_5$ is alkyl; or $R_4$ and $R_5$ together with the carbon atom to which they are attached form a carbonyl group;
$R_6$ is hydrogen, —$CO_2H$ or tetrazolyl;
$R_7$ is hydrogen, 7—tetrazolyl or 7—$CO_2H$;
X is

where $R_6'$ is hydrogen, —$CO_2H$ or tetrazolyl; or —N; and the double bond is present.

3. A compound of claim 1 wherein
$R_1$ is n-butyl;
$R_2$ is hydrogen, —$CF_3$ or chloro and $R_3$ is —$CO_2R_{17}$;
$R_4$ is hydrogen and $R_5$ is methyl; or $R_4$ and $R_5$ together with the carbon atom to which they are attached form a carbonyl group;
$R_6$ is tetrazolyl;
$R_7$ is hydrogen;
X is

where $R_6'$ is hydrogen; and the double bond is present; and connection from the dihydropyrimidinyl portion is via the para-position of the benzene ring.

4. A compound of claim 1 having the name 2-Butyl-3-[[4-[2-(2H-tetrazol-5-yl)-1H-indol-1-yl]phenyl]methyl]-4(3H)-quinazolinone, or a pharmaceutically acceptable salt thereof.

5. A compound of claim 1 having the name 2-Butyl-6-chloro-1,4-dihydro-4,4-dimethyl-1-]]4-[2-(2H-tetrazol-5-yl)-1H-indol-1-yl)phenyl]methyl]-5-pyrimidinecarboxylic acid, ethyl ester, or a pharmaceutically acceptable salt thereof.

6. A pharmaceutical composition comprising a compound of claim 1 and a pharmaceutically acceptable carrier.

7. A method for treating hypertension comprising administering to a mammalian specie in need thereof a therapeutically effective amount of a composition of claim 6.

* * * * *